United States Patent [19]
Isaacson et al.

[11] Patent Number: 5,800,349
[45] Date of Patent: Sep. 1, 1998

[54] OFFSET PULSE OXIMETER SENSOR

[75] Inventors: Philip O. Isaacson, Chanhassen; David W. Gadtke, Plymouth, both of Minn.

[73] Assignee: Nonin Medical, Inc., Plymouth, Minn.

[21] Appl. No.: 970,232

[22] Filed: Nov. 14, 1997

Related U.S. Application Data

[63] Continuation of Ser. No. 730,444, Oct. 15, 1996, abandoned.

[51] Int. Cl.⁶ ........................................ A61B 5/00
[52] U.S. Cl. ................. 600/323; 600/328; 600/500; 600/502
[58] Field of Search ........................ 600/500, 502, 600/310, 322, 323, 326, 340, 344, 473, 476

[56] References Cited

U.S. PATENT DOCUMENTS

| | | |
|---|---|---|
| Re. 33,643 | 7/1991 | Isaacson et al. . |
| 4,167,331 | 9/1979 | Nielsen . |
| 4,266,554 | 5/1981 | Hamaguri . |
| 4,586,513 | 5/1986 | Hamaguri . |
| 4,623,248 | 11/1986 | Sperinde . |
| 4,700,708 | 10/1987 | New, Jr. et al. . |
| 4,714,080 | 12/1987 | Edgar, Jr. et al. . |
| 4,714,341 | 12/1987 | Hamaguri et al. . |
| 4,784,150 | 11/1988 | Voorhies et al. . |
| 4,796,636 | 1/1989 | Branstetter et al. . |
| 4,805,623 | 2/1989 | Jobsis . |
| 4,807,631 | 2/1989 | Hersh et al. . |
| 4,819,752 | 4/1989 | Zelin . |
| 4,822,568 | 4/1989 | Tomita . |
| 4,824,242 | 4/1989 | Frick et al. . |
| 4,859,057 | 8/1989 | Taylor et al. ............... 128/633 |
| 4,869,253 | 9/1989 | Craig, Jr. et al. . |
| 4,869,254 | 9/1989 | Stone et al. . |
| 4,880,304 | 11/1989 | Jaeb et al. ................. 128/633 |
| 4,928,692 | 5/1990 | Goodman et al. . |
| 5,028,787 | 7/1991 | Rosenthal et al. . |
| 5,048,524 | 9/1991 | Bailey . |
| 5,080,098 | 1/1992 | Willett et al. .............. 128/633 |
| 5,119,815 | 6/1992 | Chance . |
| 5,188,108 | 2/1993 | Secker ........................ 128/633 |
| 5,219,400 | 6/1993 | Jacot et al. . |
| 5,246,002 | 9/1993 | Prosser . |
| 5,259,381 | 11/1993 | Cheung et al. . |
| 5,300,769 | 4/1994 | Dahlin et al. . |
| 5,313,940 | 5/1994 | Fuse et al. ................. 128/664 |
| 5,348,004 | 9/1994 | Hollub . |
| 5,351,685 | 10/1994 | Potratz . |
| 5,355,882 | 10/1994 | Ukawa et al. . |
| 5,368,224 | 11/1994 | Richardson et al. . |
| 5,372,136 | 12/1994 | Steuer et al. ............... 128/633 |
| 5,379,238 | 1/1995 | Stark . |
| 5,408,998 | 4/1995 | Mersch ....................... 128/665 |
| 5,490,523 | 2/1996 | Isaacson et al. . |
| 5,503,148 | 4/1996 | Pologe et al. . |
| 5,551,422 | 9/1996 | Simonsen et al. ........... 128/664 |
| 5,553,615 | 9/1996 | Carim et al. ................ 128/664 |

*Primary Examiner*—Lee S. Cohen
*Assistant Examiner*—David M. Ruddy
*Attorney, Agent, or Firm*—Palmatier, Sjoquist, Voigt & Christensen, P.A.

[57] ABSTRACT

In accordance with the present invention, a transmittance pulse oximeter sensor having an emitter that is offset from the detector. Offsetting the emitter and detector allows more light to pass through a thin tissue pulsating arterial bed than does a vertically aligned design. The offset between the emitter and the detector increases the effective arterial blood component without increasing artifact. Thus, the arterial blood component strength relative to the artifact strength is increased resulting in an improved signal and an improved pulse oximetry reading. The offset pulse oximetry sensor is especially important in veterinary pulse oximeter applications where it is necessary to monitor small animals whose optimal pulse oximetry location is a thin tissue tongue. The offset pulse oximetry sensor is additionally important in the realm of human medicine where often the optimal position for a pulse oximeter sensor is a thin tissue ear or an infant's thin tissue finger or toe.

19 Claims, 3 Drawing Sheets

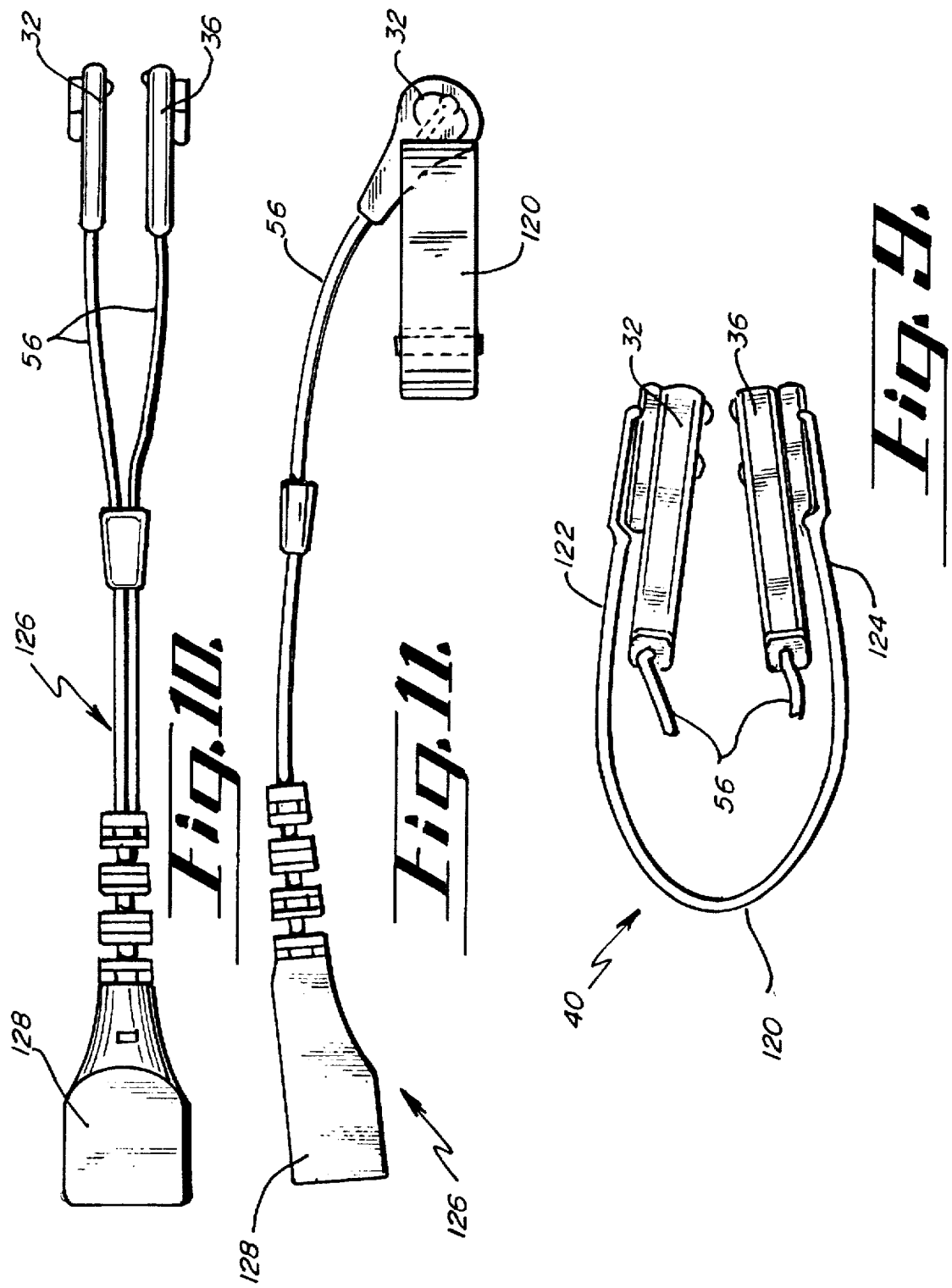

OFFSET PULSE OXIMETER SENSOR

This application is a continuation of U.S. patent application Ser. No. 08/730,444, filed Oct. 15, 1996, now abandoned.

BACKGROUND

This invention relates to medical instrumentation and, particularly, to pulse oximeter sensors.

Prior to the advent of pulse oximeters, a patient's blood oxygenation level was monitored by merely observing the patient and by arterial blood analysis which required the invasive procedure of drawing a patient's blood to acquire a lab sample for the analysis. The drawing of blood was not only uncomfortable but often painful for the patient and lab results were slow in coming. Often, too slow to provide appropriate medical attention and risk prevention.

However, pulse oximeters now permit continuous, non-invasive monitoring of a patient's blood oxygenation level. The continuity of readings allows medical personnel to quickly determine if levels are changing and whether intervening response is necessary to prevent a patient from becoming hypoxemic (a state where there is a deficiency of oxygen reaching the patient's body tissues).

In basic terms, a transmittance pulse oximeter is comprised of a sensor having an emitter and a detector both of which are coupled to electronic circuitry. The emitter is generally equipped with two separate radiation sources, preferably light-emitting diodes (LEDs), one emitting light having a wave length in the red portion of the visible spectrum and the other emanating a wave length in the infrared portion of the spectrum; the two LEDs are switched on and off sequentially. However, additional light sources may be added if it is desired to measure more than one blood constituent, i.e. more than simply the blood oxygenation level. The actual number of light sources required is one greater than the number of such constituents. The detector of the pulse oximeter sensor is generally equipped with a light-sensing device, usually a photo-diode.

Basic operation of the pulse oximeter generally consists of attaching the sensor about a tissue area including a pulsating arterial bed such as a tongue, finger or an earlobe; the emitter opposite to, and in alignment with, the detector. The red and infrared light wavelengths are then alternatively transmitted from the emitter through the pulsating arterial bed whereby a portion of each of the wavelengths is absorbed. The non-absorbed remainder of the light passes on to the detector's photo-diode which converts the light wavelength received into a corresponding electrical signal. This signal is used by the electronic circuitry to calculate the percent oxygen saturation of hemoglobin in the arterial blood, designated $S_pO_2$. Other vital information, such as a patient's pulse, may also be calculated from the signal.

As described above, it has long been the standard and accepted practice when using transmittance type pulse oximeters to oppositely align the emitter and the detector about the pulsating arterial bed. For example, U.S. Pat. No. 5,217,012 assigned to Sensor Devices, Inc. discloses an apparatus to achieve better emitter and detector alignment. The '012 patent states that

[c]onventional flexible planar sensors suffer the inherent problem of requiring precise manual alignment of the LED opposite the photosensor so that the maximum amount of light emitted by the LED is received by the photosensor . . . In the probe of the invention these problems are addressed not only by the overall U-shaped configuration of the probe 10 provided by alignment member 18, but also by the provision of position slide 22 which further facilitates proper alignment of the LED and photosensor.

(Col. 4, lines 44–66). Additionally, instructions for sensor application from Nellcor Inc., recommends that the emitter and detector be aligned; "apply the sensor to a recommended site; ensure that the LEDs and the light detector are opposite one another, on either side of an arteriolar bed." *Nellcor Troubleshooting Guide for Optical Interference*, PO 5/pg. 3 (1987). Additional patents depicting transmittance pulse oximeters wherein the emitter is aligned with the detector are U.S. Pat. No. 4,773,422, reissued as Re. Pat. No. 33,643, FIG. 1 and U.S. Pat. No. 5,490,523, FIG. 7.

The high-tech circuitry of pulse oximeters insures quality and accuracy of readings by compensating for extraneous error inducing factors. For instance, it is important that a pulse oximeter use only readings of variable absorption by the arterial blood of the red and infrared wavelengths in order to obtain a correct calculation. Thus, constant absorption by arterial blood as well as absorption by venous blood and absorption by tissue are eliminated from calculations. Further compensations built into pulse oximeters include, but are not limited to, such factors as accounting for background light interference and accounting for varying attenuation signals due to patient skin color.

As medical personnel became aware of the great utility of pulse oximeters, the demand for the devices grew. As demand grew, a great number of manufacturers entered the market adding new features and options to the device. Thus, pulse emitters have come from more cumbersome stand-alone devices to self-contained, battery operated, finger clip pulse oximeters (see applicant's U.S. Pat. No. 5,490,523). Various types of sensors have also been developed and include transmittance sensors, wherein the emitter and detector are oppositely aligned, comprised of rigid clips as well as flexible, reusable adhesive sensors and flexible, disposable adhesive sensors. Reflectance sensors are also available; reflectance sensors use the emitter and detector in a side-by-side configuration, as opposed to opposite alignment. The reflectance detector is able to detect light scattered along the tissue surface. Reflectance sensors are generally applied to the forehead.

Thus, pulse oximeters are now in wide use across the country in hospitals, rescue vehicles, and even individual homes. The use of pulse oximeters has also recently crossed the line from human medicine to veterinary medicine. However, the quest to obtain optimal use of pulse oximeters in the veterinary field has brought new, previously unaddressed problems to the forefront of pulse oximeter technology. Because cats, dogs and horses, the most commonly monitored animals, vary significantly in size, weight, shape, color, and fur density compared to the relatively minimal variation in fingers and toes in the human population, the tongue has evolved as one of the prime pulse oximetry sensor locations. Thus, when monitoring an animal a transmittance sensor is placed on the tongue, the emitter and detector as usual located opposite to but in alignment with each other. Pointedly, Sensor Devices Inc., depicts in its operating instructions for its SDI Vet/Ox #4402 that the emitter and detector are oppositely aligned (Operating Instructions, *SDI Vet/Ox #4402 Operation Manual*, 20 (December 1993)). Thus, verifying that the veterinary field has indeed followed the standard procedures utilized in human medicine requiring that the emitter of a transmittance pulse oximeter sensor be oppositely aligned with the detector.

The tongue has proven to be an adequate sensor site for oppositely aligned transmittance sensors in many instances including horses or large to medium size dogs. However, on small dogs and most cats the tongue is so thin that the amount of arterial blood passing between the aligned emitter and detector is too small to enable proper measurement of the percent oxygen saturation of hemoglobin in the arterial blood. Similar problems have also noticeably arisen in humans where pulse oximetry measurements are taken on thin tissue areas such as the ear or an infant's finger or toe. Attempts at solving these thin tissue measurement problems have included using electronic amplification of the signal from the detector as a means to compensate for poor signals from the thin tissue areas. The electronic amplification does result in an increase of the arterial blood component but unfortunately, also increases artifact resulting in a signal which can be too noisy to measure $S_pO_2$ accurately.

Thus, in view of the above, what is needed is a pulse oximeter sensor that can be used on thin tissue areas of animals and humans and that can produce proper, accurate oximetry readings from the thin tissue area.

SUMMARY

In accordance with the present invention, a transmittance pulse oximeter sensor having an emitter that is offset from the detector. Offsetting the emitter and detector allows the light to pass through a larger distance in a thin tissue pulsating arterial bed than does a vertically aligned design. The offset between the emitter and the detector increases the effective arterial blood component without increasing artifact. Thus, the arterial blood component strength relative to the artifact strength is increased resulting in an improved signal and an improved pulse oximetry reading. The offset pulse oximetry sensor is especially important in veterinary pulse oximeter applications where it is necessary to monitor small animals whose optimal pulse oximetry location is a thin tissue tongue. The offset pulse oximetry sensor is additionally important in the realm of human medicine where often the optimal position for a pulse oximeter sensor is a thin tissue ear or an infant's thin tissue finger or toe.

It is a principle object of the present invention to provide a new and improved pulse oximeter for thin tissue areas of relatively simple and inexpensive design, construction, and operation, which is safe and durable and which fulfills the intended purpose without fear of injury to animals or humans and/or damage to property.

It is another principle object of the present invention to provide a new and improved pulse oximeter for thin tissue areas which may be easily cleaned for reuse in measuring the percent oxygen saturation of hemoglobin in the arterial blood of an animal or a person.

It is still another principle object of the present invention to provide a new and improved pulse oximeter for thin tissue areas which may be amenable to the convenient receipt of maintenance and/or calibration.

It is still another principle object of the present invention to provide a new and improved pulse oximeter for thin tissue areas where the positioning of the emitter and detector may be easily and conveniently adjusted dependent upon the thickness of the tissue to be monitored during a medical or veterinary procedure.

It is still another principle object of the present invention to provide a new and improved pulse oximeter for thin tissue areas which includes an offset between the emitter and detector for the enhancement of monitoring of the percent oxygen saturation of hemoglobin in the arterial blood of an animal and/or human.

It is still another principle object of the present invention to provide a new and improved pulse oximeter which may be easily manipulated by an individual for engagement to the thin tissue area of an animal and/or human for monitoring the percent oxygen saturation of hemoglobin in the arterial blood during medical or veterinarian procedures.

It is a another principle object of the present invention to provide a pulse oximeter sensor that can be used to effectively and accurately monitor blood oxygenation levels of thin tissue pulsating arterial beds.

It is a another principle object of the present invention to provide a pulse oximeter sensor that is appropriate for use in both the fields of human medicine and veterinary medicine.

It is another principle object of the present invention is to provide a pulse oximeter sensor that is economical to produce and buy.

Still another object of the invention is to provide a pulse oximeter sensor that is simple design as well as easy to use and maintain.

A feature of the present invention includes a pulse oximeter sensor which is offset with respect to the positioning of an emitter of light for measurement and/or monitoring of the percent oxygen saturation of hemoglobin in the arterial blood of a thin tissue area.

Another feature of the present invention includes a pulsating and/or alternating light or radiation source in the infrared and red frequency wavelengths utilized to monitor the percent oxygen saturation of hemoglobin in the arterial blood of a thin tissue area during a medical or veterinary procedure.

Still another feature of the present invention includes a housing for releasably gripping a thin tissue area during a medical or veterinary procedure for monitoring the percent oxygen saturation of hemoglobin in the arterial blood of an individual and/or animal.

Still another feature of the present invention includes a gripper including a means for gripping, a first housing, a second housing, and a means for pivoting interconnecting the first and second housings for pivoting of the first and second housings relative to each other to releasably grip a thin tissue area during a medical or veterinary procedure for monitoring the percent oxygen saturation of hemoglobin in the arterial blood of an animal and/or individual.

Still another feature of the present invention includes a pulse oximeter having a means for sensing and determining the percent oxygen saturation of hemoglobin in the arterial blood within a thin tissue area as positioned between the gripper.

Still another feature of the present invention includes a display means in communication with the pulse oximeter means for displaying the sensed percent oxygen saturation level of hemoglobin in the arterial blood within a thin tissue area.

An advantage of the present invention is the provision of enhanced effective arterial blood component measurement capabilities for thin tissue areas without a corresponding increase in artifact.

DRAWINGS

These and other features, aspects, and advantages of the present invention will become better understood with regard to the following description, appended claims, and accompanying drawings where:

FIG. 1 s a depiction of a prior art pulse oximeter sensor i which the emitter and detector are in alignment about a tissue pulsating arterial bed;

FIG. 9 is an alternative view of a gripper;

FIG. 10 is a detail side view of the emitter and detector engaged to a cable; and FIG. 11 is a detail top view of the emitter and detector engaged to a cable and to a housing.

DETAILED DESCRIPTION

Figure 1:
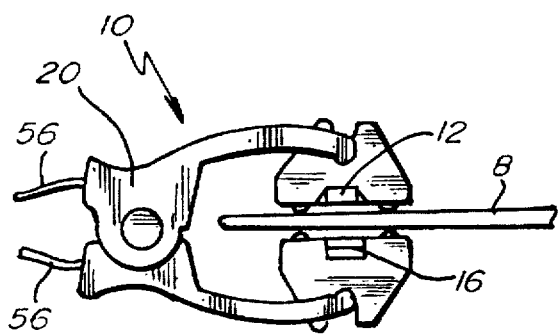

FIG. 1 depicts a standard prior art device; an oppositely aligned pulse oximeter sensor similar to those described in the background. As can be seen, the prior art pulse oximeter sensor 10 utilizes an emitter 12, which optimally contains a red and an infrared LED (neither is shown). The emitter 12 sends light through the pulsating arterial bed, in this case a larger animal's tongue to the detector 16, which optimally contains a photo diode (not shown). The emitter 12 and detector 16 are oppositely aligned with each other. The sensor 10 further comprises a clamp 20 that is adapted to hold the emitter 12 and detector 16 in position about the thick tissue area.

Figure 2:
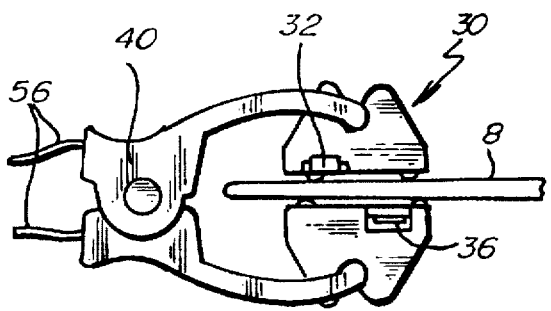
FIG. 2 is a depiction of the invention, namely, a pulse oximeter sensor with the emitter and detector in misalignment or offset from each other about a thin tissue pulsating arterial bed, namely, a small animal's tongue.

FIG. 2 depicts an offset pulse oximeter sensor 30. The offset pulse oximeter sensor 30 also contains an emitter 32, which optimally contains a red and an infrared LED (not shown). The emitter 32 may alternatively send wavelengths of infrared and red light through the pulsating arterial bed, in this case a small animal's thin tissue tongue. The light travels through the thin tissue to the offset detector 36, which optimally contains a photo diode (not shown). By offsetting the emitter and the detector, the light passes through more of the thin tissue than in the vertically-aligned design of FIG. 1. Such an arrangement increases the effective arterial blood component without increasing artifact. Thus, the arterial blood component strength relative to the artifact strength is increased resulting in an improved signal and a more accurate oximeter reading than previously available. Additionally, as was shown in the prior art of FIG. 1, the sensor further comprises a gripper 40 that is adapted to hold the emitter 32 and detector 36 in an offset position about the thin tissue area.

Light, which may alternatively be of the infrared and/or red wavelengths generated by the emitter 32 normally has a primary beam pattern area, or an area of dispersion or diffusion, which may be conical, oval, or circular in shape. The primary beam pattern area or area of illumination of infrared and/or red wavelength light is thereby established.

Figure 7:
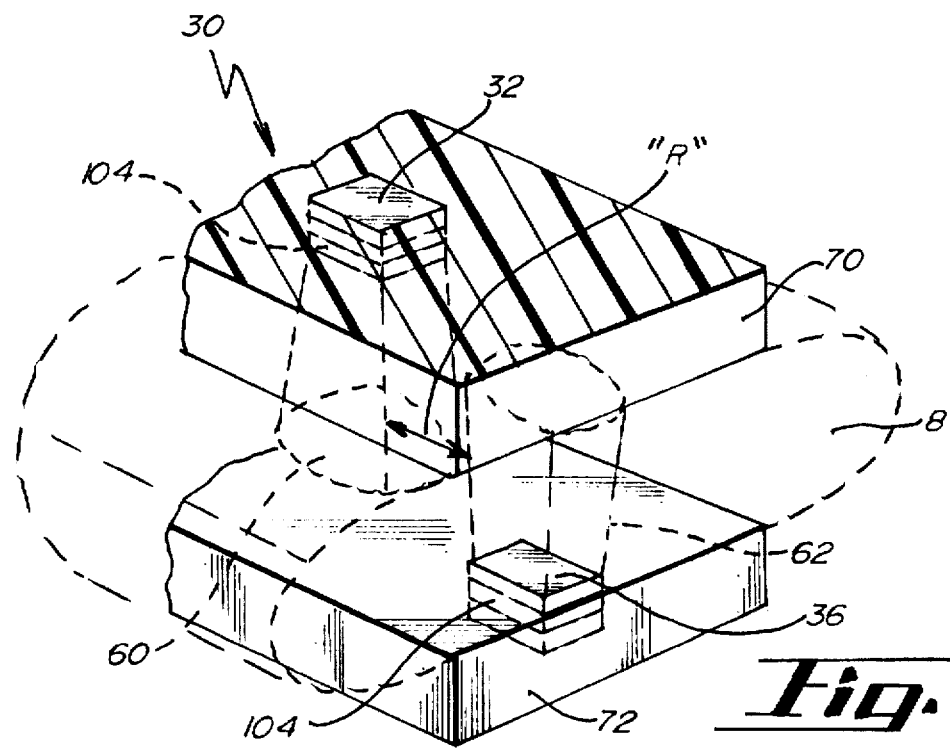
FIG. 7 is an exploded view of the offset pulse oximeter showing the area of illumination for the emitter and the effective detection area for the detector and a tongue in phantom line.

This area of illumination is referred to by numeral 60 as indicated by the dashed line on the bottom of the tongue 8. (FIG. 7)

The detector 36 has a preferred effective detection area proximate to the underside of the tongue 8 referred to by the numeral 62. (FIG. 7)

In general, the primary beam pattern area or area of illumination 60 and the primary effective detection area 62 do not intersect, touch, or overlap when the first and second housings 70, 72 respectively of the offset pulse oximeter 30 are retracted into a position for the receipt of a tongue 8. A sufficient distance of offset between the emitter 32 and detector 36 is required to separate the primary area of illumination 60 from the primary effective detection area 62 during use of the offset pulse oximeter 30. In general, the primary beam pattern area or the area of illumination 60 and the primary effective detection area 62 are slightly larger in size than the respective emitter 32 or detector 36 due to the natural diffusion of the light. It should be noted that light originating from the emitter 32 diffuses and is transmitted through a thin tissue area beyond the primary beam pattern area or area of illumination 60 for detection by the detector 36. Otherwise, the offset between the emitter 32 and the detector 36 would prevent operation of the offset pulse oximeter 30.

The measurement capabilities of the percent oxygen saturation levels of hemoglobin in the arterial blood within thin tissue areas is decreased if an overlap between the primary area of illumination 60 and the primary effective detection area 62 occurs. The performance of an offset pulse oximeter 30 is thereby reduced to the normal performance level of a pulse oximeter 10 having an aligned emitter 32 and detector 36.

The placement of an emitter 32 within a first housing 70 and the corresponding placement of the detector 36 within the second housing 72, which positions the primary area of illumination 60 adjacent to, but not in overlap with, the primary effective detection area 62, has the disadvantage of reducing the ability of an offset pulse oximeter 30 to measure percent oxygen saturation levels of the hemoglobin in the arterial blood to the performance of a normal aligned emitter 32 and detector 36. Alternatively the positioning of the primary area of illumination 60 adjacent to, but not in overlap with, the primary effective detection area 62 provides an insignificant improvement in the performance of the measurement capabilities of the offset pulse oximeter 30 over a conventional design.

The placement of an emitter 32 within the first housing 70 and the corresponding placement of the detector 36 within the second housing 72 which separates the primary area of illumination 60 approximately two tenths of one inch from the primary effective detection area 62 enhances the effective measurement capabilities of percent oxygen saturation of hemoglobin in the arterial blood of thin tissue areas for a pulse oximeter without increasing artifact.

The range of separation distance "R" on FIG. 7 which exists between the primary area of illumination 60 and the primary effective detection area 62 may vary considerably dependent upon the thickness of the thin tissue area to be monitored. Preferably, the value of the range of separation distance "R" between the primary area of illumination 60 and the primary effective detection area 62 will exceed zero and be less than two inches for thin tissue applications. A range of separation distance "R" of two tenths of one inch has been determined to perform adequately for enhanced measurement of the percent oxygen saturation levels for hemoglobin in the arterial blood for a thin tissue area by a pulse oximeter.

It should be noted that as the thickness of a thin tissue area is increased, that the separation distance "R" between the primary area of illumination 60 and the primary effective detection area 62 may be decreased for the provision of enhanced percent oxygen saturation of hemoglobin measurements. It should also be noted that at some point that the thickness of the tissue to be monitored has a sufficient dimension where an offset between the emitter 32 and the detector 36 provides marginal benefit in the measurement of percent oxygen saturation levels of hemoglobin in the arterial blood as compared to a pulse oximeter 10 having an aligned emitter 32 and detector 36. It has been determined that the tongue thickness of a forty-seven pound german shorthair canine is sufficient to provide minimal benefits of percent oxygen saturation of hemoglobin in the arterial blood measurements for a pulse oximeter 30 having an offset emitter 32 and detector 36.

It should also be noted that the separation distance "R" between the primary area of illumination 60 and the primary effective detection area 62 may be significantly increased above two tenths of one inch for enhancement of the performance of the pulse oximeter 30 for the measurement of the percent oxygen saturation of hemoglobin in the arterial blood measurements of thin tissue areas for small felines and dogs. It should also be noted that at some point that the separation distance "R" between the primary area of illumination 60 and the primary effective detection area 62 may become so large that passage and detection of light is deterred, thereby reducing the performance of a pulse oximeter 30 having an offset emitter 32 and detector 36 which in turn necessitates the placement of the emitter 32 and detector 36 in a closer proximity to each other.

It should also be noted that as the thickness of the tissue surrounding the pulsating arterial bed increases that the advantages provided by the offset pulse oximeter sensor 30 are reduced. Likewise, as the emitter 32 and detector 36 of the offset pulse oximeter sensor 30 are placed either in very close proximity, or in wide separation, the accuracy and reliability of the pulse oximetry readings from a thin tissue pulsating arterial bed are reduced. The range of optimal offset distance between the emitter and detector varies with the thickness of the thin tissue area.

It is of further note that use of the offset pulse oximeter sensor 30 on a thin tissue area virtually eliminates problems with an oximeter's signal to noise ratio. Commonly, oppositely aligned emitters and detectors were recommended because misalignment or offset on a thick tissue area would decrease the absolute amount of light received by the detector reducing the signal to noise ratio and creating an inaccurate pulse oximeter reading. However, when dealing with an offset emitter 32 and detector 36 on a thin tissue pulsating arterial bed, the signal to noise ratio remains virtually unaffected because thin tissue areas, such as a small animal's tongue, are nearly transparent to the red and infrared light used in the emitter 32.

Figure 8:
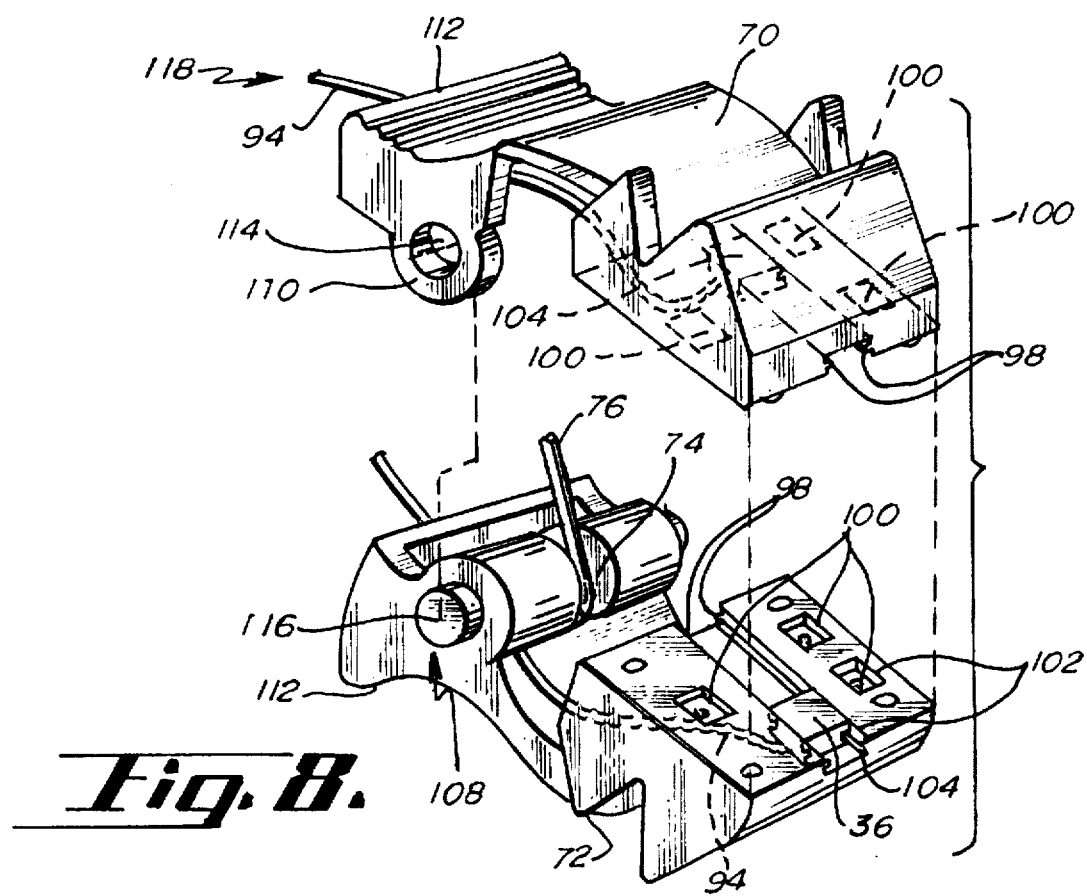
FIG. 8 is an isometric exploded view of a gripper.

The offset pulse oximeter 30 may take the form of a first housing 70 connected to a second housing 72 via a spring 74 and means for pivoting 108. (FIG. 8) The means for pivoting 108 may be formed of a pair of pivot tabs 110 which may depend from the first housing 70 proximate to the grasping portion 112. Each pivot tab 110 may include a pivot aperture 114. The means for pivoting 108 may further include a pair of pivot pins 116 which extend outwardly from the second housing 72 proximate to the grasping portion 112. (FIG. 8)

Alternatively, the means for pivoting 110 may be formed of a shaft which traverses through apertures integral to each of the first and second housings 70, 72 respectively. Alternatively, bolts and/or screws may form the means for pivoting 108 provided that the grasping portions 112 of each of the first and second housings 70, 72 respectively may be manipulated together for release or engagement of the offset pulse oximeter 30 to a thin tissue area. The pivot pins 116 of the second housing 72 preferably engage the pivot apertures 114 Of the first housing 70 to provide a pivoting relationship therebetween allowing for the manipulation of the gripper 40 via the compression of the grasping portions 112 toward each other.

The second housing 72 may include the spring 74 which in turn may include an end 76. The end 76 may be adapted for engagement to the first housing 70 proximate to the grasping portion 112 for urging of the gripper 40 into a closed configuration where the first housing 70 is proximate to the second housing 72. Alternatively, the spring 74 may be comprised of two generally u-shaped spring elements which are themselves connected in a side-by-side manner including a short spring element section. Alternatively, the spring 74 may be a tension spring as preferred by an individual. A short spring element section may be positioned within a groove which may be integral to the bottom of the first housing 70. The first housing 70 may also include indents which may pivotally receive tabs of the second housing 72. The spring 74 allows the first housing 70 and the second housing 72 to pivot and/or separate relative to one another. The means for pivoting 108 and the spring 74 preferably provides an urging force which manipulates the first and second housing 70, 72 respectively into a closed position about a thin tissue area.

The first housing 70 and the second housing 72 may include a contour for the receipt of the thin tissue area such as a tongue 8, finger, or ear for positioning of the emitter 32 and detector 36 within a desired location for reading of the pulse and/or blood oxygen saturation of a patient and/or animal.

The first housing 70 may include or be electrically connected to a means for display via a means for communication 118. The means for communication 118 may be used to communicate the generated electrical signals from the detector 36 to the means for computation. The generated electrical signals may then be processed for calculation of the pulse rate and/or percent oxygen saturation of hemoglobin for an animal or patient ($S_pO_2$). The means for communication 118 may be formed of ribbon cable 94 or wire at the preference of an individual. It should be noted that the means for display and the means for computation may be integral to the first and second housings 70, 72 or may be independent thereof at the discretion of an individual.

A means for generating power is also preferably electrically connected to the first housing 70 and to the emitter 32 in order to provide the power source for the provision of light utilized to measure the percent of oxygen saturation of hemoglobin. Electrical power may be transmitted from the means for generating power via the means for communication 118 which may be ribbon cable 94 or wire at the discretion of an individual. The means for generating power may be integral to, or independent from, the first and second housings 70, 72 at the discretion of an individual. The means for generating power may be standard electrical current as available from an electrical fixture outlet or batteries at the discretion of an individual.

The emitter 32 may preferably include a ribbon cable 94 which may be engaged to the first housing 70 for provision of electrical power from the means for generating power for the transmittal of alternating wavelengths of infrared and red light. The detector 36 may also include a ribbon cable 94 which is preferably attached to the second housing 72 for providing electrical communication with the means for computation for communication of received signals utilized for measuring the percent oxygen saturation of hemoglobin in the arterial blood of a thin tissue area.

The spring 74 may be releasably connected to the first and second housing 70, 72. The spring 74 may be designed to allow separation of the first housing 70 from the second housing 72. The first housing 70 may thereby be separated from the second housing 72 to facilitate cleaning. Alternatively, the pivot tabs 110 may be urged outwardly to disengage the pivot pins 116 from the pivot apertures 114 to permit the separation of the first housing 70 from the second housing 72. The spring 74 may then be separated from the first housing 70 permitting the elements of the offset pulse oximeter 30 to be cleaned by an individual.

The first housing 70 may include guide tracks 98 or apertures 100 which are adapted to either fixedly or releasably engagement and positioning of the emitter 32 in any location as desired by an individual. The guide tracks 98 or apertures 100 provide the offset pulse oximeter 30 with a means for positioning 102 of the emitter 32 to the first housing 70. The means for positioning 102 may also include ridges or positioning tabs if a guide track 98 is utilized. The emitter 32 may also include mating tabs 104 which are adapted for sliding engagement within the guide tracks 98 for positioning of the emitter 32 in a desired location with respect to the first housing 70. It should also be noted that the emitter 32 or the first housing 70 may include an affixation member which may be utilized to releasably or fixedly position the emitter 32 in a desired location with respect to the first housing 70.

It should also be noted that the second housing 72 may also include guide tracks 98, apertures, 100, and/or a means for positioning 102 for the releasable or fixed engagement of the detector 36 to the second housing 72. Please note that the guide tracks 98, apertures 100, and/or means for positioning 102, may be identical between the first housing 70 and the second housing 72 or alternatively, any combination of guide tracks 98, apertures 100, and/or means for positioning 102 may be incorporated into either the first housing 70 or second housing 72 at the preference of an individual. Please also note that the detector 36 may also include mating tabs 104 for releasable or fixed engagement to guide tracks 98. In addition, the detector 36 may include an affixation member for the provision of adjustable positioning of the detector 36 on the second housing 72. An individual may thereby select a desired distance of separation "R" between the primary area of illumination 60 and the primary effective detection area 62 during use of the offset pulse oximeter 30.

The offset configuration of the emitter 32 and detector 36 may be easily incorporated into other standard sensor configurations or grippers 40. As depicted in FIG. 9, the housing 120 may be generally unshaped having an emitter engagement portion 122 and a detector engagement portion 124 which may be adapted for either fixed or releasable receipt of the emitter 32 and detector 36 respectively. This embodiment of the gripper 40 includes a housing 120 which, in an at rest configuration, positions the emitter engagement portion 122 into contact with the detector engagement portion 124. The emitter engagement portion 122 and the detector engagement portion 124 are required to be separated from positioning of a thin tissue area between the offset emitter 32 and detector 36. In this embodiment, the housing 120 includes a resiliently pliable feature for facilitation of engagement and retention of a thin tissue area to be monitored by the offset pulse oximeter 30. It should be noted that the gripper 40, depicted in FIG. 9, is adapted to hold the emitter 32 and detector 36 in the offset configuration. This gripper 40 is also equipped with a wire cable 56 to direct the detector signal back to a standard free-standing, portable, or hand-held pulse oximeter (not shown). This gripper 40 may be manufactured to be either reusable, and thus, capable of being cleaned, or disposable, at the preference of an individual.

FIG. 10 depicts a side view of the detection assembly 126 which may include the emitter 32 and detector 36. A wire cable 56 may be engaged to the emitter 32 and detector 36. The wire cables 56 may also be connected to a plug 128. The plug 128 is preferably adapted for engagement to a standard free standing, portable, and/or hand held pulse oximeter at the discretion of an individual.

FIG. 11 is a top view of the detector assembly 126 immediately prior to the engagement of, or immediately following the separation of, an emitter 32 from a housing 120. In this embodiment, the housing 120 is preferably adapted to slidably receive the emitter 32 for positioning in an offset location with respect to a detector 36.

Figure 3:
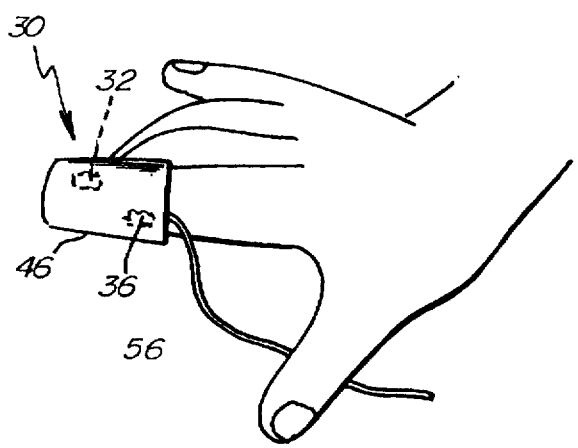
FIG. 3 is a depiction of an offset pulse oximeter sensor contained in a finger clip attached to an infant's thin tissue finger.

The offset configuration of the emitter 32 and detector 36 shown in FIG. 2 may easily be incorporated into other standard sensor configurations or gripping means, 46, 48, 50, 52. For example, FIG. 3 shows an offset emitter 32 and detector 36 incorporated into a standard finger clip sensor 46 that is attached to an infant's thin tissue finger. The finger clip 46 may be attached by wire cable 56 to a portable or hand-held pulse oximeter (not shown) or the finger clip 46 itself may contain a battery operated pulse oximeter, see applicant's U.S. Pat. No. 5,490,523, Finger Clip Pulse Oximeter. The finger clip 46 is usually made of plastic or other rigid, durable material. Note that either variation of the finger clip 46 is reusable and easily cleaned with mild detergent or alcohol.

Figure 4:
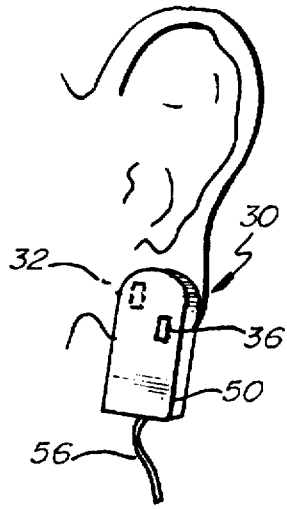
FIG. 4 is a depiction of an offset pulse oximeter sensor contained in an ear clip attached to an adult's thin tissue earlobe.

FIG. 4 exhibits how the emitter 32 and detector 36 of FIG. 2 can be easily incorporated into a standard ear clip sensor 48 which is adapted to hold the emitter 32 and detector 36 in the offset configuration. The ear clip 48, attached to an adult's thin tissue earlobe, is equipped with wire cable 56 to be connected to a free-standing, portable or hand-held pulse oximeter for appropriate oxygen saturation readings. The ear clip 48, like the finger clip 46 is usually made of plastic or other rigid, durable material. Likewise, it is reusable and easily cleaned with mild detergent or alcohol.

Figure 5:
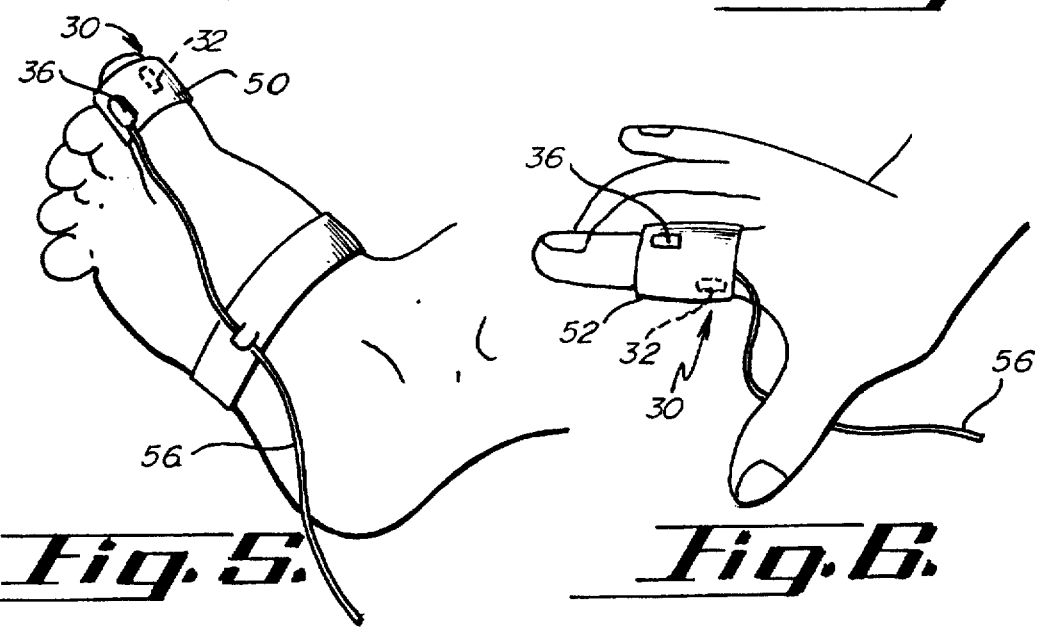
FIG. 5 is a depiction of an offset pulse oximeter sensor contained in a flexible toe wrap attached to an infant's thin tissue toe.

FIG. 5 depicts the emitter 32 and detector 36 of FIG. 2 as incorporated into a standard toe wrap sensor 50 adapted to hold the emitter 32 and detector 36 in the offset configuration. The toe wrap 50 is wrapped about an infant's thin tissue toe. Similar to the configurations above, the toe wrap 50 is also equipped with a wire cable 56 to direct the detector signal back to a standard free-standing, portable or hand-held pulse oximeter (not shown). The toe wrap 50 is generally made a combination of materials that are generally soft and flexible so as to be easily wrapped about a small toe yet rigid enough to support and hold in position the emitter 32 and detector 36. The toe wrap 50 may be manufactured to be either reusable, and thus, capable of being cleaned, or disposable.

Figure 6:
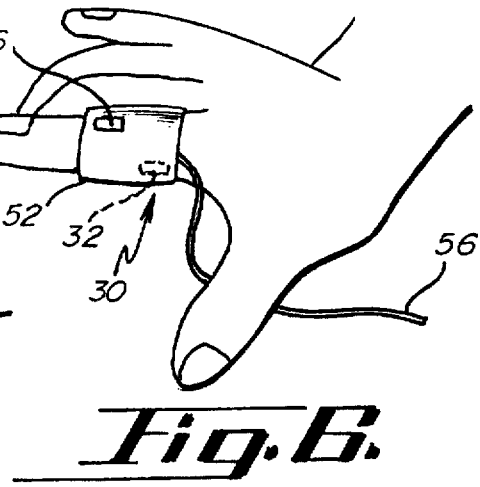
FIG. 6 is a depiction of an offset pulse oximeter sensor contained in a flexible finger wrap attached to an infant's thin tissue finger.

FIG. 6 depicts the emitter 32 and detector 36 of FIG. 2 as incorporated into a standard finger wrap sensor 52 adapted to hold the emitter 32 and detector 36 in the offset configuration. The finger wrap 52 is wrapped about an infant's thin tissue finger. Once again, similar to the configurations above, the finger wrap 52 is equipped with a wire cable 56 capable of transmitting the detector's signal back to a standard free-standing, portable or hand-held pulse oximeter (not shown). Like the toe wrap 50, the finger wrap 52 is generally made of a combination of materials that are soft and flexible so as to easily be wrapped about a small infant's finger yet rigid enough to support and hold in position the emitter 32 and detector 36. The finger wrap 52 may also be manufactured to be either reusable, and thus, capable of being cleaned, or disposable.

It is important to note that any and all of the sensor configurations or gripping means described above may be equipped with additional radiation sources such that blood constituents beyond that of $S_PO_2$ may be measured. As stated in the background, the actual number of light sources required is one greater than the number of such constituents.

The present invention may be embodied in other specific forms without departing from the spirit of the essential attributes thereof; therefore, the illustrated embodiment should be considered in all respects as illustrative and not restrictive, reference being made to the appended claims rather than to the foregoing description to indicate the scope of the invention.

We claim:

1. An offset transmittance pulse oximeter sensor for measuring the oxygenation level of blood by passing light of at least two wavelengths through tissue containing blood and measuring the absorption of the light by blood constituents in the blood at the at least two wavelengths, comprising:

(a) a housing having an emitter engagement portion and a detector engagement portion;

(b) an emitter engaged to said emitter engagement portion, said emitter for introducing light of at least two wavelengths into a first tissue surface, said light of at least two wavelengths adapted to traverse said first tissue surface along a substantially identical path;

(c) a detector engaged to said detector engagement portion, said detector for measuring the light emanating from a second tissue surface, said detector being positioned with respect to said emitter so as to be offset along the second tissue surface with respect to the position of said emitter along said first tissue surface during use such that said light from the emitter traverses a substantially non-perpendicular path through the tissue to the detector; and (d) a means for measuring the amount of light absorbed by blood constituents in blood within the tissue along the substantially identical path for the at least two wavelengths between the detector and emitter.

2. The offset pulse oximeter sensor of claim 1 wherein said emitter provides an area of illumination.

3. The offset pulse oximeter sensor of claim 2 wherein said detector has an effective detection area.

4. The offset pulse oximeter sensor of claim 3 wherein said area of illumination is separated from said effective detection area by a separation distance.

5. The offset pulse oximeter sensor of claim 4 wherein said separation distance exceeds zero inches and is less than two inches.

6. The offset pulse oximeter sensor of claim 4 wherein said separation distance is at least one tenth of one inch.

7. The offset pulse oximeter sensor of claim 1, said housing comprising a means for positioning permitting adjustable attachment of said emitter in a desired location with respect to said emitter engagement portion.

8. The offset pulse oximeter sensor of claim 7, said means for positioning comprising guide tracks on said emitter engagement portion, said guide tracks adapted for the adjustable positioning of said emitter with respect to said emitter engagement portion.

9. The offset pulse oximeter sensor of claim 7, said means for positioning comprising a plurality of apertures adapted for releasable receipt of said emitter for the adjustable positioning of said emitter with respect to said emitter engagement portion.

10. The offset pulse oximeter sensor according to claim 7, said emitter further comprising an affixation member for adjustable positioning of said emitter with respect to said means for positioning.

11. The offset pulse oximeter sensor according to claim 8 said emitter further comprising mating tabs for engagement to said guide tracks for adjustable positioning of said emitter with respect to said emitter engagement portion.

12. The offset pulse oximeter sensor according to claim 11, said emitter further comprising an affixation member for adjustable and releasable positioning of said emitter with respect to said guide tracks and said emitter engagement portion.

13. The offset pulse oximeter sensor of claim 1, said detector engagement portion comprising a means for positioning permitting adjustable attachment of said detector in a desired location with respect to said detector engagement portion.

14. The offset pulse oximeter sensor of claim 13, said means for positioning, comprising guide tracks on said detector engagement portion, said guide tracks adapted for the adjustable positioning of said detector with respect to said detector engagement portion.

15. The offset pulse oximeter sensor of claim 13, said means for positioning comprising a plurality of apertures adapted for releasable receipt of said detector for the adjustable positioning of said detector with respect to said detector engagement portion.

16. The offset pulse oximeter sensor according to claim 13, said detector further comprising an affixation member for adjustable positioning of said detector with respect to said means for positioning.

17. The offset pulse oximeter sensor according to claim 14, said detector further comprising mating tabs for engagement to said guide tracks for adjustable positioning of said detector with respect to said detector engagement portion.

18. The offset pulse oximeter sensor according to claim 17, said detector further comprising an affixation member for adjustable and releasable positioning of said detector with respect to said guide tracks and said detector engagement portion.

19. An offset transmittance pulse oximeter sensor for measuring the pulse and/or the present oxygen saturation of hemoglobin of arterial blood in thin tissue areas by passing light of at least two wavelengths through tissue containing blood and measuring the absorption of the light by blood constituents in the blood at the at least two wavelengths, said offset pulse oximeter sensor comprising:

(a) a gripper comprising a first housing and second housing;

(b) an emitter engaged to said first housing, said emitter transmitting light of at least two wavelengths and establishing an area of illumination, said emitter for introducing the light into a first tissue surface, said light of at least two wavelengths adapted to traverse said first tissue surface along a substantially identical path;

(c) a detector for detecting light and for measuring the amount of light absorbed at the at least two wavelengths by blood constituents in the blood within the tissue along the substantially identical path for the two wavelengths between the detector and emitter and generating electrical signals, said detector engaged to said second housing, said detector having an effective detection area, said effective detection area being separated from said area of illumination by a separation distance of at least one twentieth of an inch, said detector for measuring the light emanating from a second tissue surface, said detector being positioned with respect to said emitter so as to be offset along the second tissue surface with respect to the position of said emitter on said first tissue surfaces during use such that light from the emitter traverses the substantially non-perpendicular path through the tissue to the detector;

(d) a means for displaying the measured pulse or percent oxygen saturation of hemoglobin in the arterial blood;

(e) a means for generating power through said emitter and said detector;

(f) a means for computation for calculating the pulse and/or the percent oxygen saturation of hemoglobin in arterial blood from said electrical signals generated by said detector; and (g) a means for communication connected to said emitter, said detector, and said means for computation.

* * * * *